United States Patent [19]

Yoshikawa et al.

[11] 3,933,736

[45] Jan. 20, 1976

[54] POLYOLEFIN COMPOSITION

[75] Inventors: Toshio Yoshikawa; Nagayoshi Sakamoto; Tomitada Nagamori, all of Ichihara, Japan

[73] Assignee: UBE Industries, Ltd., Yamaguchi, Japan

[22] Filed: Aug. 14, 1974

[21] Appl. No.: 497,302

[30] Foreign Application Priority Data

Feb. 26, 1974  Japan................................ 49-21945

[52] U.S. Cl............................................ 260/45.8 R
[51] Int. Cl.²........................................ C08L 23/00
[58] Field of Search ........... 260/45.8 N, 45.8 NZ, 260/45.8 NT

[56] References Cited
UNITED STATES PATENTS

| | | | |
|---|---|---|---|
| 3,734,926 | 5/1973 | Dexter | 260/45.8 N |
| 3,746,721 | 7/1973 | Stephen | 260/45.8 N |
| 3,821,161 | 6/1974 | Stephen | 260/45.8 N |

*Primary Examiner*—M. J. Welsh
*Assistant Examiner*—William E. Parker
*Attorney, Agent, or Firm*—Flynn & Frishauf

[57] ABSTRACT

A stabilized polyolefin composition having resistance against deterioration caused by contact with heavy metals such as copper which comprises 100 weight parts of polyolefin and 0.001–5 weight parts of N-(salicyloylamino)imide is disclosed.

19 Claims, 18 Drawing Figures

POLYOLEFIN COMPOSITION

This invention relates to a polyolefin composition having resistance against deterioration caused by contact with heavy metals.

Heretofore, such polyolefins as polyethylene, polypropylene, polybutene and the like have been employed in the form of several kinds of molded products manufactured by several kinds of molding processes in the wide field owing to their excellent physical or chemical characteristics. However, as is commonly known, if a polyolefin is employed with no additives, it will be deteriorated by heat, light or oxygen during processing or its use. In order to prevent its deterioration, several kinds of anti-oxidizing agents have been developed and employed.

Yet, in cases where polyolefins cannot be kept from contact with such heavy metals as copper, iron, nickel and the like, for instance, in cases of covering polyolefin over copper wire, plating polyolefin with heavy metals, coloring polyolefin by pigments containing heavy metals and the like, the use of the aforementioned general anti-oxidizing agents can hardly bring about resistance against deterioration caused by contact with heavy metals.

Further, if liquid amorphous polyolefin may possibly be touched with copper, for instance, if liquid amorphous polyolefin is employed as a insulating oil for cables, there is required resistance against deterioration caused by contact with copper. Yet, the mere use of the aforementioned general anti-oxidizing agents cannot meet the above requirement.

In view of the above, there has been broadly employed anti-deteriorating agents such as oxamide and oxanilide Japanese Patent Publn. No. 14484/62), N-salicylidene-N'-salicylhydrazide (Japanese Patent Publn. No. 12293/65), oxalo-bis(benzylidenehydrazide) U.S. Pat. No. 3,440,210) and the like which were provided for the purposes of imparting to polyolefins resistance against deterioration caused by contact with heavy metals. Yet, these agents cannot likewise be mentioned as agents satisfying the requirement of anti-deteriorating effect.

Therefore, an object of this invention is to provide a polyolefin composition having excellent resistance against deterioration caused by contact with heavy metals. Another object is to provide a stabilized polyolefin composition which can be employed especially for covering of copper wire. A further object of this invention is to provide a liquid amorphous polyolefin composition having excellent resistance against said deterioration. Other objects of this invention will be obvious from the contents of the specification hereinafter disclosed.

The present inventors studied for the purpose of providing polyolefin compositions having resistance against deterioration caused by contact with heavy metals, and have completed this invention based on the fact that the following compositions show excellent anti-deteriorating effect against deterioration caused by contact with heavy metals:

A polyolefin composition which comprises 100 weight parts of polyolefin and 0.001 ~ 5 weight parts of a N-(salicyloylamino)-imide represented by the formula (1)

or

(2)

in which A represents a group in which $R^1 - R^4$ represent hydrogen atoms, halogen atoms, nitro groups, amino groups, carboxyl groups, hydroxyl groups, phenyl groups, phenylthio groups, or straight or branched alkyl, halogenated alkyl, alkoxyl, alkylthio, alkylamino or acylamino groups each having 1 to 5 carbon atoms, and B represents a group in which Q represents an oxygen atom, a sulfur atom, a methylene group, a carbonyl group, a phenylene group, a phthaloyl group, an isophthaloyl group or a terephthaloyl group, and n is an integer of 0 or 1 or

Polyolefins of the compositions according to this invention may be exemplified by homopolymers or copolymers of olefins such as ethylene, propylene, butene-1, isobutene, pentene-1, 4-methylpentene-1 and the like, copolymers of these olefins and an alkylester of an unsaturated carboxylic acid such as ethyl acrylate or a vinylester of saturated carboxylic acid such as vinyl acetate, mixtures of these polymers, liquid amorphous polypropylene and liquid amorphous polybutene.

The anti-deteriorating agent contained in the compositions of the present invention may be synthesized by reacting salicyloylhydrazine with a cyclic acid anhydride represented by the formula:

(3)

or (4)

in which A and B are the same as defined above in the presence of a solvent. The solvent to be used in the reaction may preferably be a solvent capable of dissolving salicyloylhydrazine, a cyclic acid anhydride and N-(salicyloylamino)imide, and may be, for instance, N,N-dialkylacylamide such as N,N-dimethylformamide and N,N-dimethylacetamide, or an aliphatic acid such as formic acid and acetic acid, but is not limited to these examples.

The aforementioned salicyloylhydrazine and a cyclic acid anhydride may preferably be in the ratio of equivalent molar amounts in the synthesis of a N-(salicyloylamino)imide represented by the formula (1), and in the molar ratio of 2 : 1 (former : latter) in the synthesis of a N-(salicyloylamino)imide represented by the formula (2). However, the present reaction may proceed in the absence of these conditions.

The reaction temperature and the reaction period may vary depending on the kinds of cyclic acid anhydrides, solvents and the like. Any temperature below a boiling point of the solvent used may be adopted, and, in general, a temperature in the range of 20° to 120°C may be adopted. The reaction period may generally be between 10 minutes and 15 hours.

The resulting anti-deteriorating agent can easily be recovered, after completion of the reaction, by removing the solvent under reduced pressure from the reaction mixture and by washing the residue with an alcohol such as methanol and ethanol or by cooling the reaction mixture to room temperature, pouring this into a large amount of water and collecting the obtained solid by filtration.

The anti-deteriorating agents represented by the aforementioned formula (1) are concretely exemplified by:
N-(salicyloylamino)phthalimide, 3-chloro-N-(salicyloylamino)phthalimide, 4-chloro-N-(salicyloylamino)phthalimide, 3,6-dichloro-N-(salicyloylamino)phthalimide, 4,5-dichloro-N-(salicyloylamino)phthalimide, 3,4,5,6-tetrachloro-N-(salicyloylamino)phthalimide, 3,6-dibromo-N-(salicyloylamino)phthalimide, 3,4,5,6-tetrabromo-N-(salicyloylamino)phthalimide, 3-iodo-N-(salicyloylamino)phthalimide, 4-iodo-N-(salicyloylamino) phthalimide, 4,5-diiodo-N-(salicyloylamino)phthalimide, 3,4,5,6-tetraiodo-N-(salicyloylamino)phthalimide, 3-fluoro-N-(salicyloylamino)phthalimide, 3,6-difluoro-N-(salicyloylamino) phthalimide, 3,4,5,6-tetrafluoro-N-(salicyloylamino)phthalimide, 3-nitro-N-(salicyloylamino)phthalimide, 4-nitro-N-(salicyloylamino)phthalimide, 3-amino-N-(salicyloylamino)phthalimide, 4-amino-N-(salicyloylamino)phthalimide, 4-carboxy-N-(salicyloylamino)phthalimide, 4-hydroxy-N-(salicyloylamino)phthalimide, 3,6-dihydroxy-N-(salicyloylamino)phthalimide, 3,6-dihydroxy-4-methyl-N-(salicyloylamino)phthalimide, 3-hydroxy-4-methoxy-N-(salicyloylamino)phthalimide, 3-hydroxy-5-methoxy-N-(salicyloylamino)phthalimide, 3-hydroxy-4,6-dimethyl-N-(salicyloylamino)phthalimide, 6-hydroxy-4-methoxy-3-methyl-N-(salicyloylamino)phthalimide, 3-(phenylthio)-N-(salicyloylamino)phthalimide, 3-methyl-5-(phenylthio)-N-(salicyloylamino)phthalimide, 3-methyl-N-(salicyloylamino)phthalimide, 4-methyl-N-(salicyloylamino)phthalimide, 3,4-dimethyl-N-(salicyloylamino)phthalimide, 3,6-dimethyl-N-(salicyloylamino)phthalimide, 4,5-dimethyl-N-(salicyloylamino)phthalimide, 3-propyl-N-(salicyloylamino) phthalimide, 6-isobutyl-3,4-dimethyl-N-(salicyloylamino) phthalimide, 3-methyl-6-(methylthio)-N-(salicyloylamino) phthalimide, 5-(ethylthio)-3-methyl-N-(salicyloylamino) phthalimide, 3-(ethylthio)-6-methyl-N-(salicyloylamino)-phthalimide, 3-ethyl-6-(ethylthio)-N-(salicyloylamino)-phthalimide, 4,6-dimethoxy-3-methyl-N-(salicyloylamino)-phthalimide, 3-methoxy-4,6-dimethyl-N-(salicyloylamino)-phthalimide, 4-isopropyl-3,5,6-trimethoxy-N-phthalimide, (salicyloylamino) phthalimide, 3-(dibromomethyl)-N-(salicyloylamino)phthalimide, 3-methoxy-N-(salicyloylamino)-phthalimide, 4-methoxy-N-(salicyloylamino)phthalimide, 3,4-dimethoxy-N-(salicyloylamino) phthalimide, 3,6-dimethoxy-N-(salicyloylamino)phthalimide, 4,5-dimethoxy-N-(salicyloylamino)phthalimide, 3,5-dimethoxy-4-methyl-N-(salicyloylamino)phthalimide, 3-(methylthio)-N-(salicyloylamino)phthalimide, 3-(ethylthio)-N-(salicyloylamino) phthalimide, 3-(propylthio)-N-(salicyloylamino)phthalimide, 3-acetamido-N-(salicyloylamino)phthalimide, 4-acetamido-N-(salicyloylamino)phthalimide, 3-(dimethylamino)-N-

(salicyloylamino)phthalimide, 3-(isopropylamino)-N-(salicyloylamino)-phthalimide, N-(salicyloylamino)-1,8-naphthalimide, N-(salicyloylamino)-chlorendic imide, N-(salicyloylamino)-cis-4-cyclohexene- 1,2-dicarboxylimide and N-(salicyloylamino)-cyclohexane-1,2-dicarboxylimide.

The anti-deteriorating agents represented by the aforementioned formula (2) are concretely exemplified by:

4,4'- bis[N-(salicyloylamino)phthalimide], 3,4'-bis[N-(salicyloylamino)phthalimide], 4,4'-oxybis[N-(salicyloylamino)-phthalimide], 3,3'-methylenebis[N-(salicyloylamino)phthalimide], 4,4'-methylenebis[N-(salicyloylamino)phthalimide], 4,4'-carbonylbis[N-(salicyloylamino)phthalimide], 4,4'-(p-phenylene)-bis[N-(salicyloylamino)phthalimide], 4,4'-isophthaloylbis[N-(salicyloylamino)phthalimide], 4,4'-terephthaloylbis[N-(salicyloylamino)phthalimide] and N,N'-bis(-salicyloylamino)-1,2,4,5-benzenetetracarboxyl-1,2,4,5-diimide.

In the compositions of the present invention, an amount of mixing or compounding of the anti-deteriorating agent is between 0.001 ~ 5 weight parts, preferably 0.05 ~ 2 weight parts per 100 weight parts of polyolefin by weight. An amount of mixing or compounding less than the above-mentioned 0.001 weight part cannot show enough anti-deteriorating effect and an amount of mixing or compounding more than 5 weight parts cannot show any further anti-deteriorating effect.

Every process adequate for preparation of a homogeneous composition may be adopted to a process for mixing or compounding of the aforesaid anti-deteriorating agent into a polyolefin, for example, a process which comprises dissolving the antideteriorating agent in a low-boiling solvent, mixing the solution with a polyolefin and removing the solvent by evaporation; a process which comprises heating a polyolefin above its melting point and then mixing a the anti-deteriorating agent therewith; or a process which comprises mixing polyolefin with the anti-deteriorating agent by means of Bumbury's mixer or Henschel mixer.

Further, in accordance with the prior art, one or several kinds of antioxidants are incorporated into the compositions of the present invention. The antioxidant is employed in an amount of 0.001 ~ 5 weight parts based on 100 weight parts of polyolefin and may be a phenolic antioxidant, for instance, 2,6-di-tert-butyl-p-cresol, 2,6-di-tert-butylphenol, 4,4'-methylenebis(2,6-di-tert-butylphenol), 4,4'-methylenebis(3-methyl-6-tert-butylphenol), 4,4'-thiobis(2,6-di-tert-butylphenol), 4,4'-thiobis(2-methyl-6-tert-butylphenol), 4,4'-thiobis(3-methyl-6-tert-butylphenol), 6-(4-hydroxy-3,5-di-tertbutylanilino)-2,4-bis(n-octylthio)-1,3,5-triazine, tetrakis-[methylene 3-(3,5-di-tert-butyl-4-hydroxyphenyl)propionate]-methane, octadecyl 3-(3,5-di-tert-butyl-4-hydroxyphenyl)-propionate, 1,1,3-tris(2-methyl-4-hydroxy-5-tert-butylphenyl)-butane, 2,2'-methylenebis(4-methyl-6-tert-butylphenol), 4,4'-butylidenebis(3-methyl-6-tert-butylphenol), 1,3,5-trimethyl-2,4,6-tris(3,5-di-tert-butyl-4-hydroxybenxyl)benzene and the like.

In addition, the anti-deteriorating agent used in the present invention may be employed together with known stabilizing agents, dispersing agents, plasticizers, fillers and/or the like. These known stabilizing agents may be exemplified by dialkyl 3,3'- thiodipropionate such as didodecyl 3,3'-thiodipropionate and dioctadecyl 3,3'-thiodipropionate and organo phosphrus compounds such as trilauryl trithiophosphite, trilauryl phosphite and tris(nonylphenyl)-phosphite.

Synthesis examples of the anti-deteriorating agents contained in the composition of the present invention will be shown below. Salicyloylhydrazines employed in these syntheses examples were prepared by the following steps:

25 weight parts of methyl salicylate and 20 weight parts of hydrazine hydrated (85 %) were heated under reflux for 4 hours in the presence of 100 weight parts of ethanol; after removal of the ethanol under reduced pressure, the residue was cooled; the precipitate thus obtained was collected by filtration and washed with distilled water; and the resulting residue was recrystallized from ethanol to yield the desired compound, m.p. 147°C.

SYNTHESIS EXAMPLE 1

Synthesis of N-(salicyloylamino)phthalimide

Figure 1:
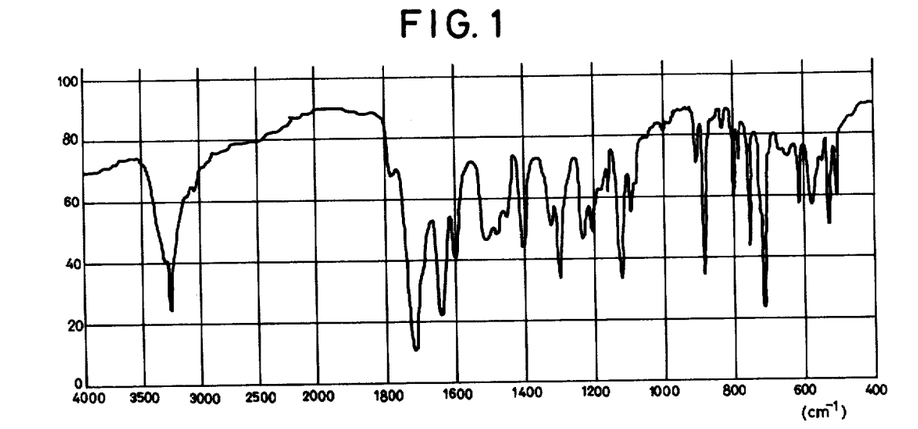
Figure 2:
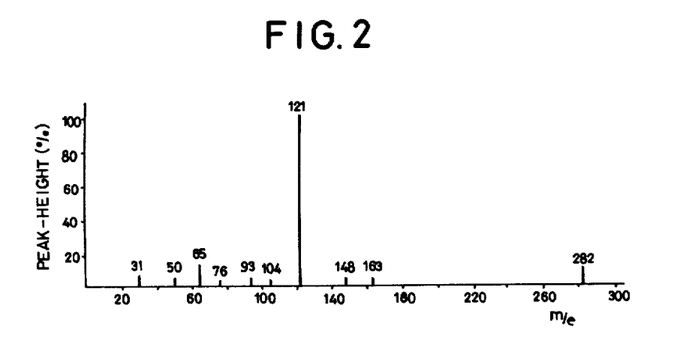

In a flask equipped with a stirrer and a thermometer were placed 2.96 g of phthalic anhydride, 3.04 g of salicyloylhydrazine and 50 ml of N,N-dimethylformamide. The reaction was carried out with stirring for 3.5 hours at a temperature kept at 83°C. After completion of the reaction, the reaction mixture was cooled to room temperature and poured into 2 liters of water to precipitate a white solid. The solid was collected by filtration, washed with ethanol and dried under reduced pressure to yield 4.1 g of a white powder, m.p. 252° – 253°C. The powder thus obtained was easily soluble in acetone at room temperature, hardly soluble in ethanol at room temperature, soluble in acetic acid, benzene and chloroform in hot states, and insoluble in ethyl ether, petroleum ether, n-hexane and carbon tetrachloride in hot states. This powder was identified as N-(salicyloylamino)phthalimide by the elemental analysis, IR spectrum (KBr tablet, the same hereinafter) (FIG. 1) and Mass spectrum (FIG. 2).

Found (%): C, 63.93; H, 3.55; N, 10.04. Calcd. for $C_{15}H_{10}N_2O_4$(%): C, 63.82; H, 3.55; N, 9.93.

SYNTHESIS EXAMPLE 2

Synthesis of N-(salicyloylamino)-cyclohexane-1,2-dicarboxylimide

Figure 3:
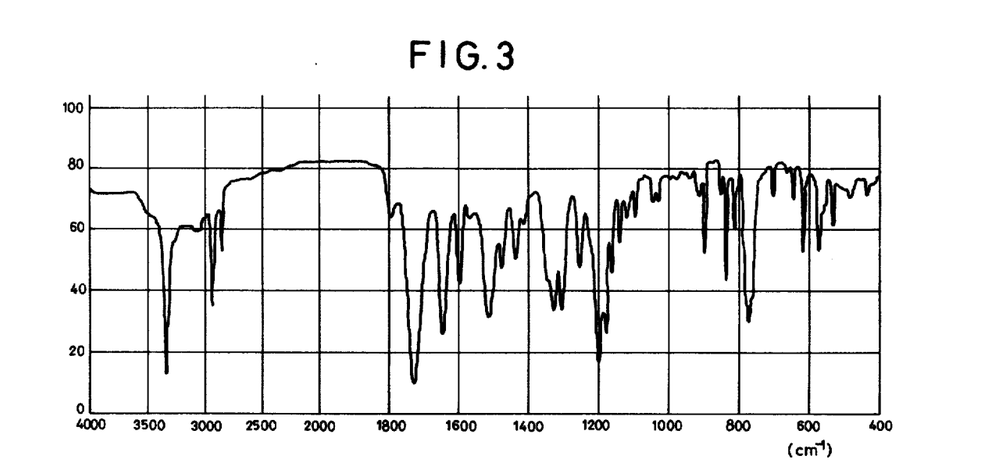
Figure 4:
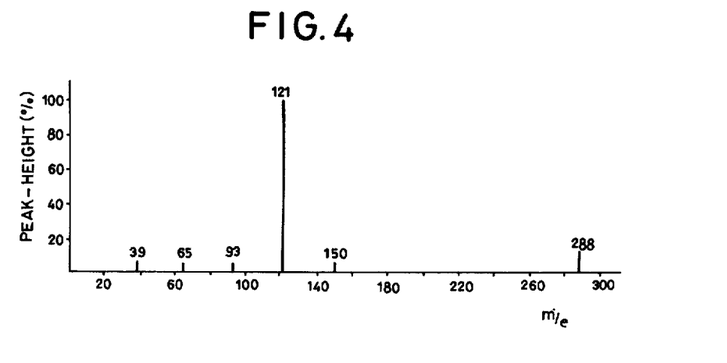

In a flask equipped with a stirrer and a thermometer were placed 3.04 g of hexahydrophthalic anhydride, 3.04 g of salicyloylhydrazine and 20 ml of N,N-dimethylformamide, and the reaction was performed with stirring for 3.5 hours at a temperature kept at 84° – 85°C. After completion of the reaction, the reaction mixture was treated in the same manner as in Synthesis example 1 to give 5.2 g of a white powder, m.p. 227°C. The obtained powder was soluble in acetone at room temperature and hardly soluble in ethanol, acetic acid, benzene, chloroform, carbon tetrachloride and petroleum ether at room temperature. This powder was identified as N-(salicyloylamino)-cyclohexane-1,2-dicarboxylimide by the elemental analysis, IR spectrum (FIG. 3) and Mass spectrum (FIG. 4).

Found (%): C, 62.27; H, 5.65; N, 9.67. Calcd. for $C_{15}H_{16}N_2O_4$(%): C, 62.50; H, 5.56; N, 9.72.

SYNTHESIS EXAMPLE 3

Synthesis of N-(salicyloylamino)-cis-4-cyclohexene-1,2-dicarboxylimide

Figure 5:
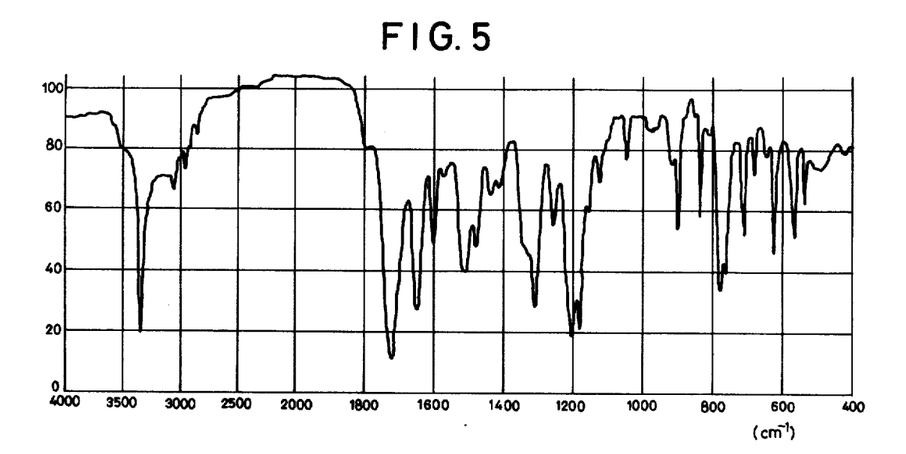
Figure 6:
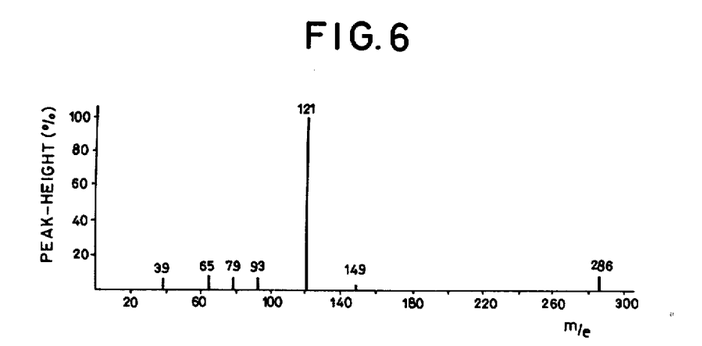

The same reaction as in Synthesis example 1 except that 3.04 g of cis-4-cyclohexene-1,2-dicarboxylic anhydride, 3.04 g of salicyloylhydrazine and 20 ml of N,N-dimethylformamide were used and 89°C of the reaction temperature and 3 hours of the reaction period were employed was carried out. The reaction mixture was then treated in the same manner as in Synthesis example 1 to give 3 g of a white powder, m.p. 192° – 192.5°C. The powder thus obtained was soluble in acetone, ethanol, acetic acid, chloroform and benzene at room temperature and insoluble in petroleum ether, ligroin, n-hexane and carbon tetrachloride in hot states. Further, the powder was identified as N-(salicyloylamino)-cis-4-cyclohexene-1,2-dicarboxylimide by the elemental analysis, IR spectrum (FIG. 5) and Mass spectrum (FIG. 6).

Found (%): C, 62.18; H, 4.77; N, 9.79. Calcd. for $C_{15}H_{14}N_2O_4$(%): C, 62.94; H, 4.90; N, 9.70.

SYNTHESIS EXAMPLE 4

Synthesis of 3,4,5,6-tetrachloro-N-(salicyloylamino)phthalimide

Figure 7:
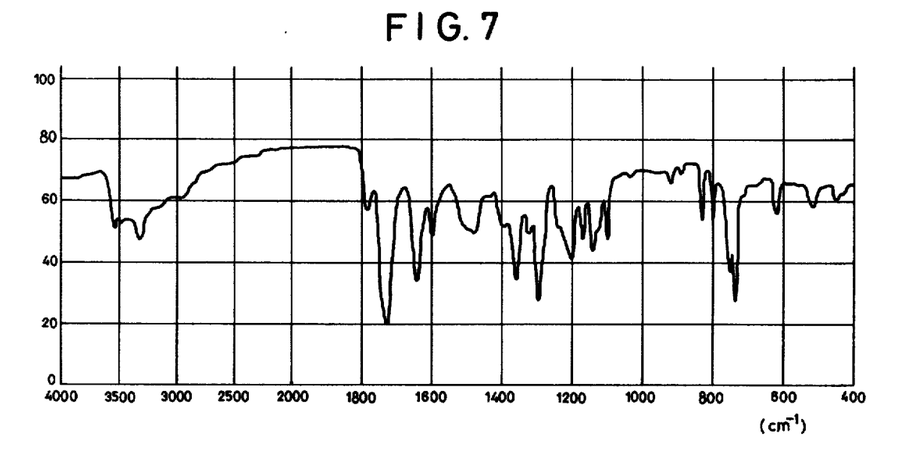
Figure 8:
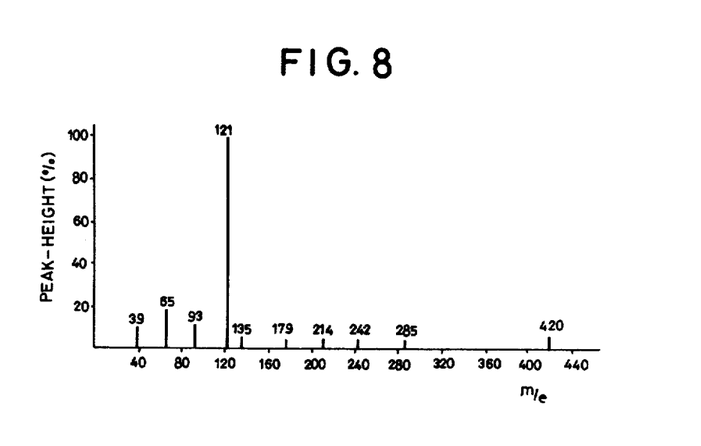

The same reaction as in Synthesis example 1 except that 2.86 g of tetrachlorophthalic anhydride, 1.52 g of salicyloylhydrazine and 10 ml of N,N-dimethylformamide were used and 85°C of the reaction temperature and 3 hours and 45 minutes of the reaction period were employed was carried out. The reaction mixture was then treated in the same manner as in Synthesis example 1 to give 3.5 g of yellow crystals, m.p. 290° – 293°C. The crystals thus obtained were soluble in acetone at room temperature, soluble in acetic acid, chloroform and ethanol in hot states and hardly soluble in benzene and carbon tetrachloride. Further, the crystals were identified as 3,4,5,6-tetrachloro-N-(salicyloylamino)phthalimide by the elemental analysis, IR spectrum (FIG. 7) and Mass spectrum (FIG. 8).

Found (%): C, 42.86; H, 1.60; N, 6.56; Cl, 32.62. Calcd. for $C_{15}H_6N_2Cl_4O_4$(%): C, 42.86; H, 1.43; N, 6.67; Cl, 33.81.

SYNTHESIS EXAMPLE 5

Synthesis of the N-(salicyloylamino)-4-carboxyphthalimide

Figure 9:
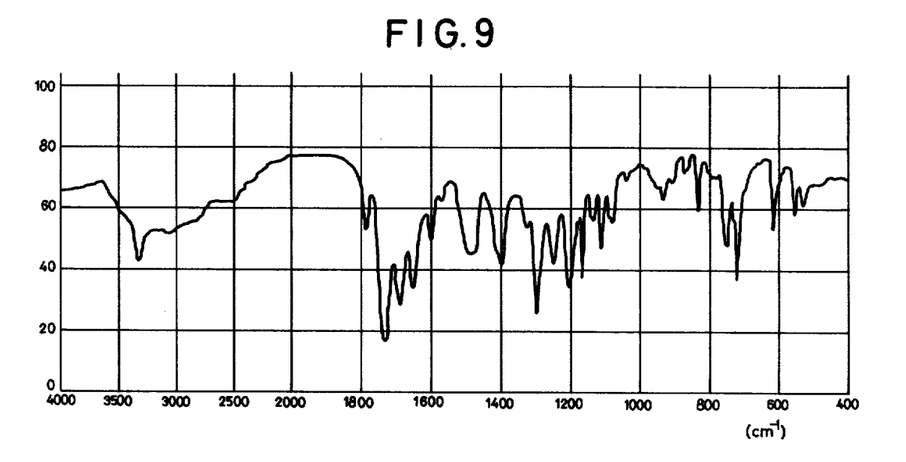
Figure 10:
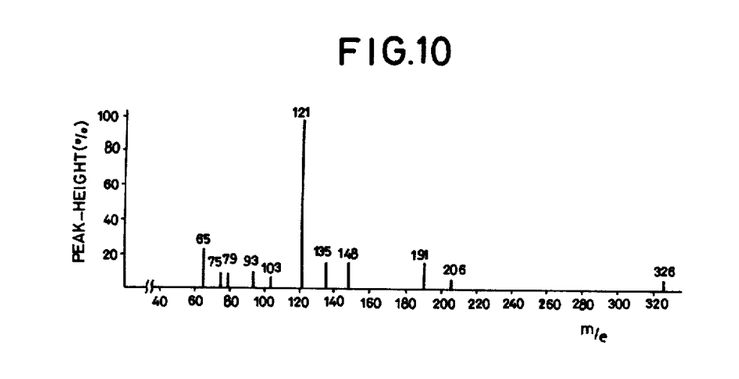

The same reaction as in Synthesis example 1 except that 1.92 g of trimellitic anhydride, 1.52 g of salicyloylhydrazine and 10 ml of N,N-dimethylformamide were used was carried out. The reaction mixture was then treated in the same manner as in Synthesis example 1 to give 2.1 g of a white powder, m.p. 288.5° – 290°C. The powder thus obtained was soluble in ethanol, acetic acid and acetone in hot states, and insoluble in chloroform and carbon tetrachloride. The powder was identified as N-(salicyloylamino)-4-carboxyphthalimide by the elemental analysis, IR spectrum (FIG. 9) and Mass spectrum (FIG. 10).

Found (%): C, 58.33; H, 3.06; N, 8.65.

Calcd. for $C_{16}H_{10}N_2O_6$(%): C, 58.90; H, 3.07; N, 8.59.

SYNTHESIS EXAMPLE 6

Synthesis of N-(salicyloylamino)-1,8-naphthalimide

Figure 11:
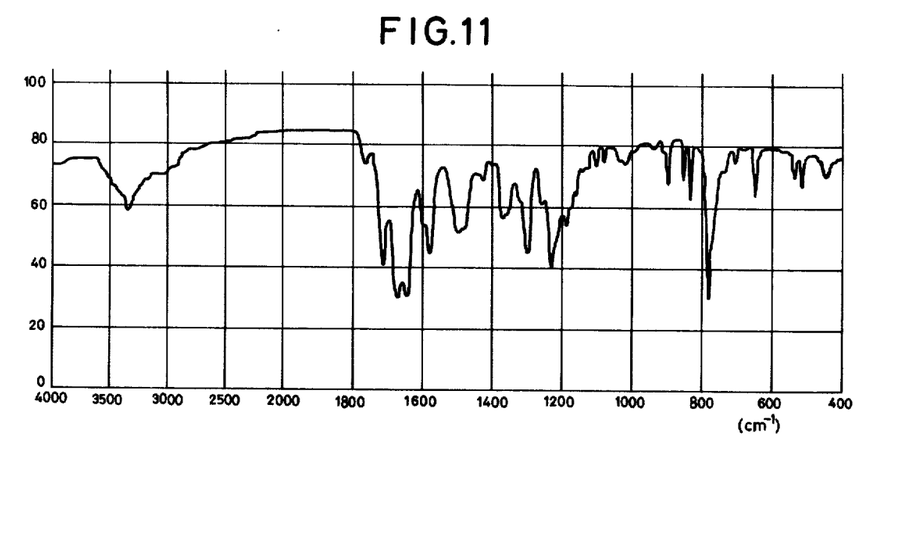
Figure 12:
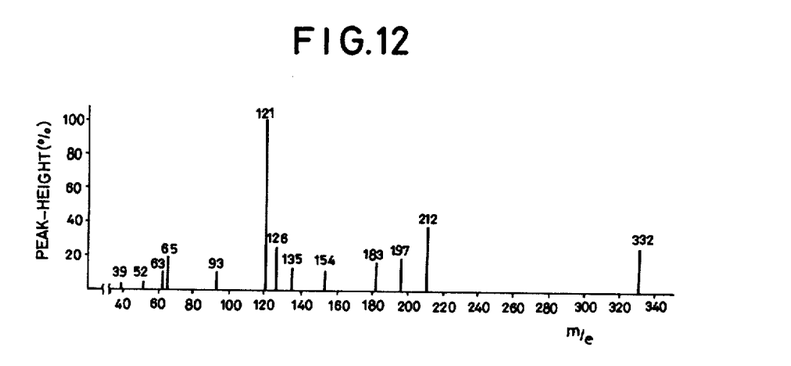

The same reaction as in Synthesis example 1 except that 1.98 g of 1,8-naphthalic anhydride, 1.52 g of salicyloylhydrazine and 20 ml of N,N-dimethylformamide were used and 81° – 83°C of the reaction temperature was employed was carried out. The reaction mixture was then treated in the same manner as in Synthesis example 1 to give 3 g of a yellow powder, m.p. 268°C. The powder thus obtained was soluble in benzene at room temperature, soluble in chloroform, acetic acid and ethanol in hot states and insoluble in n-hexane and ethyl ether. Further, the powder was identified as N-(salicyloylamino)-1,8-naphthalimide by the elemental analysis, IR spectrum (FIG. 11) and Mass spectrum (FIG. 12).

Found (%): C, 68.02; H, 3.57; N, 8.05. Calcd. for $C_{19}H_{12}N_2O_4$(%): C, 68.67; H, 3.61; N, 8.43.

SYNTHESIS EXAMPLE 7

Synthesis of N-(salicyloylamino)-chlorendic imide

Figure 13:
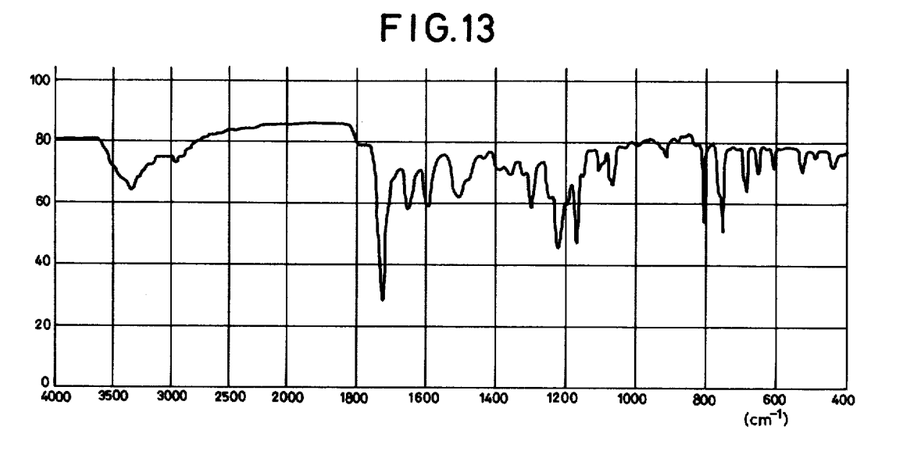
Figure 14:
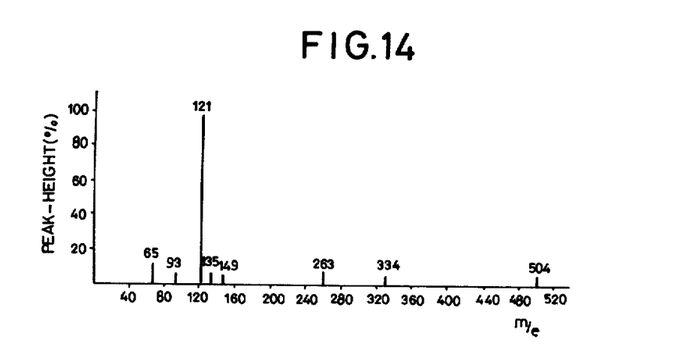

The same reaction as in Synthesis example 1 except that 3.71 g of chlorendic anhydride (1,4,5,6,7,7-hexachloro-endo-5-norbornene-2,3-dicarboxylic anhydride), 1.52 g of salicyloylhydrazine and 10 ml of N,N-dimethylformamide were used was carried out. The reaction mixture was then treated in the same manner as in Synthesis example 1 to give 1.5 g of an earth brown powder, m.p. 317°C. The powder thus obtained was soluble in chloroform, ethanol and acetone at room temperature, soluble in hot acetic acid and insoluble in benzene, carbon tetrachloride and ethyl ether. Further, the powder was identified as N-(slicyloylamino)-chlorendic imide by the elemental analysis, IR spectrum (FIG. 13) and Mass spectrum (FIG. 14).

Found (%): C, 37.80; H, 1.68; N, 5.42; Cl, 42.33. Calcd. for $C_{16}H_8N_2O_4Cl_6$ (%): C, 38.02; H, 1.58; N, 5.54; Cl, 42.18.

SYNTHESIS EXAMPLE 8

Figure 15:
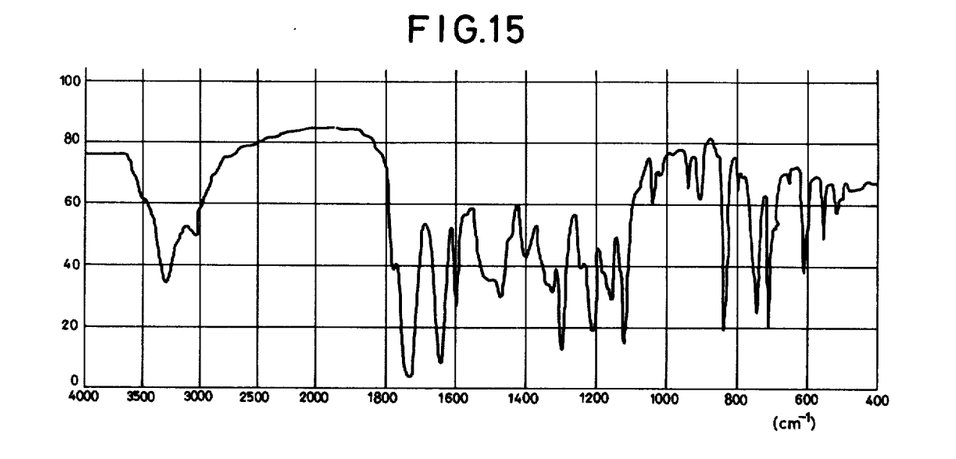
Figure 16:
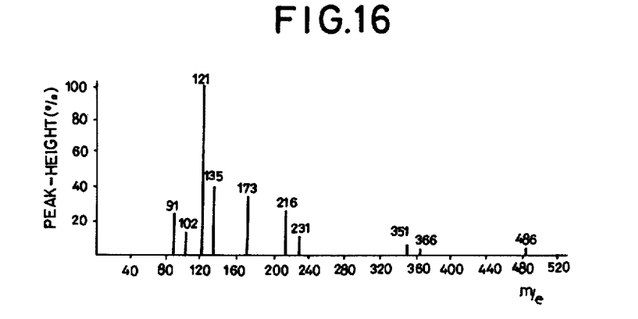

Synthesis of N,N'-bis(salicyloylamino)-1,2,4,5-benzenetetracarboxyl-1,2,4,5-diimide The same reaction as in Synthesis example 1 except that 2.0 g of pyromellitic anhydride, 3.0 g of salicyloylhydrazine and 50 ml of N,N-dimethylformamide were used was carried out. The reaction mixture was then treated in the same manner as in Synthesis example 1 to give 1.7 g of a white powder, m.p. 365° – 366°C. The powder thus obtained was hardly soluble in even ethanol, benzene, acetone, ethyl ether, carbon tetrachloride and chloroform in hot states. Further, the powder was identified as N,N'-bis(salicyloylamino)-1,2,4,5-benzenetetracarboxyl-1,2,4,5-diimide by the elemental analysis, IR spectrum (FIG. 15) and Mass spectrum (FIG. 16).

Found (%): C, 59.20; H, 2.83; N, 11.68. Calcd. for $C_{24}H_{14}N_4O_8$ (%): C, 59.26; H, 2.88; N, 11.52.

SYNTHESIS EXAMPLE 9

Synthesis of 4,4'-bis[N-(salicyloylamino)phthalimide]

Figure 17:
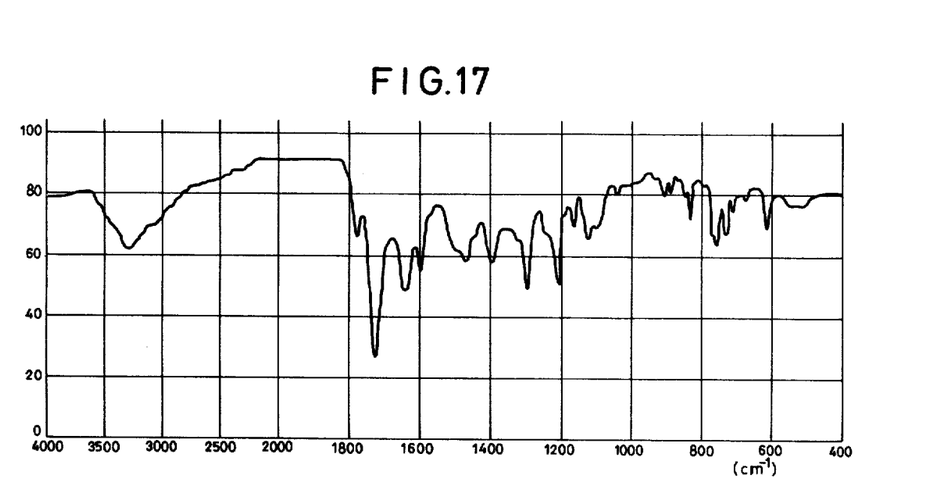

The same reaction as in Synthesis example 1 except that 2.94 g of 4,4'-di(phthalic anhydride) (or 3,4,3',4'-diphenyltetracarboxylic anhydride), 3.10 g of salicyloylhydrazine and 10 ml of N,N-dimethylformamide were used and 80°C of the reaction temperature and 5 hours of the reaction period were employed was carried out. The reaction mixture was then treated in the same manner as in Synthesis example 1 to give 3.2 g of a white powder, m.p. 345° – 347°C. The powder thus obtained was identified as 4,4'-bis[N-(salicyloylamino)phthalimide] by the elemental analysis and IR spectrum (FIG. 17).

Found (%): C, 64.44; H, 3.44; N, 9.84. Calcd. for $C_{30}H_{18}N_4O_8$ (%): C, 64.06; H, 3.20; N, 9.96.

SYNTHESIS EXAMPLE 10

Synthesis of 3,4'-bis[N-(salicyloylamino)phthalimide]

Figure 18:
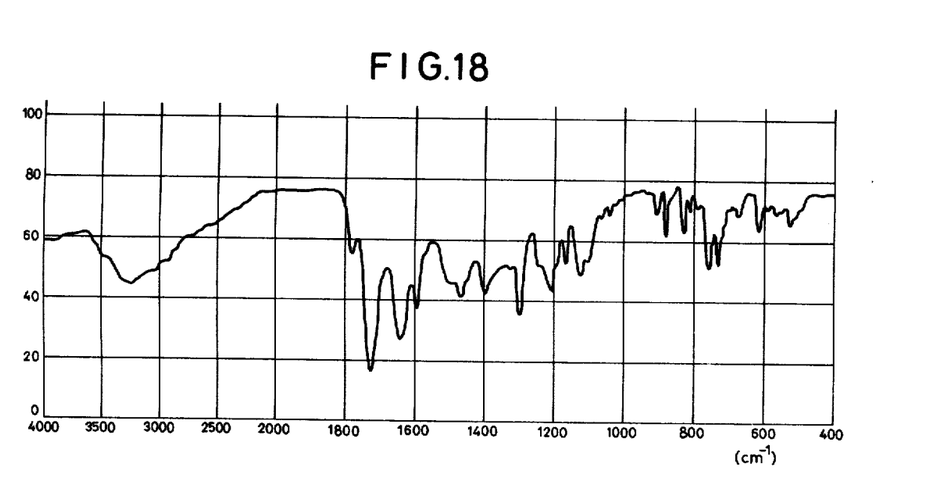

The same reaction as in Synthesis example 1 except that 2.94 g of 3,4'-di(phthalic anhydride), 3.10 g of salicyloylhydrazine and 10 ml of N,N-dimethylformamide were used and 90°C of the reaction temperature and 7 hours of the reaction period were employed was carried out. The reaction mixture was then treated in the same manner as in Synthesis example 1 to give 4.5 g of a white powder, m.p. 217°C. The powder thus obtained was soluble in acetone at room temperature, soluble in acetic acid and ethanol in hot states and insoluble in even benzene and chloroform in hot states. This powder was identified as 3,4'-bis[N-(salicyloylamino)phthalimide] by the elemental analysis and IR spectrum (FIG. 18).

Found (%): C, 64.63; H, 3.76; N, 10.55. Calcd. for $C_{30}H_{18}N_4O_8$ (%): C, 64.06; H, 3.20; N, 9.96.

The following are examples and comparative examples. The term "part" means weight part and M.I. means Melt Flow Index which was determined in accordance with ASTMD 1238. The notations shown in Examples and comparative examples mean the following compounds.

A: N-(salicyloylamino)phthalimide
B: N-(salicyloylamino)-cyclohexane-1,2-dicarboxylimide
C: N-(salicyloylamino)-cis-4-cyclohexene-1,2-dicarboxylimide
D: 3,4,5,6-tetrachloro-N-(salicyloylamino)phthalimide
E: N-(salicyloylamino)-4-carboxylphthalimide
F: N-(salicyloylamino)-1,8-naphthalimide
G: N-(salicyloylamino)-chlorendic imide
H: N,N'-bis(salicyloylamino)-1,2,4,5-benzenetetracarboxyl1,2,4,5-diimide
I: 4,4'-bis[N-(salicyloylamino)phthalimide]
J: 3,4'-bis[N-(salicyloylamino)phthalimide]
a: oxamide
b: oxanilide
c: oxalobis(benzylidenehydrazide)
d: N-salicylidene-N'-salicyloylhydrazide
e: tetrakis-[methylene 3-(3,5-di-tert-butyl-4-hydroxyphenyl)propionate]methane
f: 4,4'-thiobis(3-methyl-6-tert-butylphenol)
g: dioctadecyl-3,3'-thiodipropionic acid ester
h: trilauryltrithiophosphite
i: 1,3,5-trimethyl-2,4,6-tris(3,5-di-tert-butyl-4-hydroxybenzyl)benzene
j: 1,1,3-tris(2-methyl-4-hydroxy-5-tert-butylphenyl)butane
k: octadecyl 3-(3,5-di-tert-butyl-4-hydroxyphenyl)-propionate
l: didodecyl 3,3'-thiodipropionate
m: 2,6-di-tert-p-cresol In the above, the compounds of e, f, i, j, k and m are phenolic antioxidants.

EXAMPLES 1 TO 10

1. Preparation of test piece

Into Brabender plastograph (available from Brabender Corporation, West Germany) adjusted to 60 r.p.m. of rotation speed and a temperature of 140°C were charged 100 parts of ethylene homopolymer with no additives (M.I. = 0.2) which had been prepared by a high pressure process. Two minutes later, 0.10 part of an antioxidant, tetrakis [methylene 3-(3,5-di-tert-butyl-4-hydroxyphenyl)-propionate]methane, and 0.15 part of a compound (anti-deteriorating agent) set forth in Table 1 were added thereto. Another 2 minutes later, 0.10 part of copper stearate was added to the mixture, which was subsequently kneaded for 8 minutes. The mixture was then heated on a plate of 190°C for 1 minute and pressed at a pressure of 300 kg/cm$^2$ for 1 minute by means of a spacer to form a film having a thickness of 0.25 mm. A round film of 4 mm in its diameter was prepared by punching of the obtained film, and employed as a test piece.

2. Determination of anti-deteriorating effect

The period required for appearance of a peak showing generation of heat caused by oxidation was determined by means of Standard-Type Rapidly Fluctuating Differential Calorimeter (available from Rigaku Denki Kogyo Ltd., Japan). The calorimeter received a test piece in one sample dish and the other dish remained empty. After the atmosphere of the calorimeter was replaced with oxygen, the environmental temperature was elevated to 195°C in an instant (about 5 – 10 seconds) by means of inside heating system with flow of oxygen into the system at a rate of 180 ml/min. Subsequently, the temperature was elevated to 200°C for a period of about 30 seconds, and kept at 200°C. The period from the time when the temperature reached 200°C to the time when there appeared a peak showing generation of heat caused by oxidation of the test piece (minutes; induction period) was measured and adopted to estimate an anti-deteriorating effect.

The results obtained according to the above-mentioned process are shown in Table 1.

Table 1

| Example | Compound | Induction period (min.) |
|---------|----------|-------------------------|
| 1 | A | 59 |
| 2 | B | 65 |
| 3 | C | 58 |
| 4 | D | 48 |
| 5 | E | 29 |
| 6 | F | 52 |
| 7 | G | 42 |
| 8 | H | 33 |
| 9 | I | 35 |
| 10 | J | 30 |

COMPARATIVE EXAMPLES 1 TO 6

Test pieces were prepared by the method described in Example 1 except for using no anti-deteriorating agent and no copper stearate; using copper stearate only; or using publicly known stabilizers in the amount set forth in Table 2. Their effects were determined in the manner described in Example 1 and their results are shown in Table 2.

Table 2

| Comparative example | Kind and amount (part) of stabilizer | Amount of copper stearate (part) | Induction period (min) |
|---|---|---|---|
| 1 | — | — | 39.0 |
| 2 | — | 0.10 | 0 |
| 3 | a 0.15 | do. | 17.4 |
| 4 | b do. | do. | 20.5 |
| 5 | c do. | do. | 25.8 |
| 6 | d do. | do. | 27.3 |

EXAMPLES 11 to 20

1. Preparation of test piece

Into the same Brabender plastograph as employed in Example 1 which was adjusted to 60 r.p.m. of rotation speed and a temperature of 200°C were charged 100 parts of isotactic polypropylene with no additives (M.I. = 5). Two minutes later, 0.03 part of $e$, 0.10 part of $g$ and 0.20 part of $h$, all of which were publicly known stabilizers and, in addition, 0.5 part of the anti-deteriorating agent disclosed by the present invention which is set forth in Table 3 were added thereto. Another 2 minutes later, 1.5 parts of copper powder was added to the mixture, which was subsequently kneaded for 8 minutes. The mixture was then heated on a plate of 200°C for 1 minute and pressed at a pressure of 300 kg/cm² for 1 minute by means of a spacer to form a film having a thickness of 1.0 mm. The film thus obtained was employed as a test piece.

2. Determination of anti-deteriorating effect

The test piece was kept in Geer's oven (inside temperature: 150°C), and a period (in hours) until the test piece turned yellow and deteriorated was measured and adopted as "Heat stable duration".

The results thus obtained are shown in Table 3.

Table 3

| Example | Compound | Heat stable duration (hr) |
|---|---|---|
| 11 | A | 145 |
| 12 | B | 160 |
| 13 | C | 140 |
| 14 | D | 135 |
| 15 | E | 65 |
| 16 | F | 140 |
| 17 | G | 130 |
| 18 | H | 105 |
| 19 | I | 120 |
| 20 | J | 85 |

COMPARATIVE EXAMPLE 7

A test piece was prepared in the same manner as in Example 11 except that the publicly known stabilizer $d$ was employed in the amount of 0.5 part in place of the antideteriorating agent, A, disclosed by this invention. The test piece thus obtained was measured in its effect in the same manner as in Example 11 to show 40 hours of the heat stable duration.

EXAMPLES 21 - 32

Test pieces were prepared by the method described in Example 1 except for using anti-deteriorating agents and stabilizers (or antioxidants) described in Table 4 and also using copper stearate (0.18 part). Their effects were determined in the manner described in Example 1 and their results are shown in Table 4.

Table 4

| Example | Kind and amount (part) of anti-deteriorating agent | Kind and amount (part) of stabilizer (antioxidant) | | Induction period (min) |
|---|---|---|---|---|
| 21 | A | 0.10 | e 0.20<br>g 0.50 | 55 |
| 22 | A | 0.20 | e 0.10<br>g 0.50 | 43 |
| 23 | C | 0.10 | e 0.20<br>g 0.50 | 62 |
| 24 | C | 0.20 | e 0.10<br>g 0.50 | 48 |
| 25 | H | 0.10 | e 0.20<br>g 0.50 | 45 |
| 26 | H | 0.20 | e 0.10<br>g 0.50 | 40 |
| 27 | A | 0.10 | f 0.20<br>i 0.30 | 60 |
| 28 | A | 0.20 | f 0.20<br>i 0.20 | 60 |
| 29 | A | 0.30 | f 0.20<br>i 0.10 | 37 |
| 30 | H | 0.10 | j 0.25<br>k 0.30<br>l 0.30 | 31 |
| 31 | H | 0.20 | j 0.25<br>k 0.20<br>l 0.30 | 34 |
| 32 | H | 0.30 | j 0.25<br>k 0.10<br>l 0.30 | 33 |

COMPARATIVE EXAMPLES 8 - 15

Test pieces were prepared by the method described in Example 1 except for using anti-deteriorating agents and stabilizers (or antioxidants) described in Table 5 and using copper stearate (0.18 weight part). Their effects were determined in the manner described in Example 1 and their results are shown in Table 5.

Table 5

| Comparative example | Kind and amount (part) of anti-deteriorating agent | Kind and amount (part) of stabilizer (antioxidant) | | Induction period (min) |
|---|---|---|---|---|
| 8 | C | 0.10 | e 0.20<br>g 0.50 | 29 |
| 9 | C | 0.20 | e 0.10<br>g 0.50 | 30 |
| 10 | C | 0.10 | f 0.20<br>i 0.30 | 35 |
| 11 | C | 0.20 | f 0.20<br>i 0.20 | 23 |
| 12 | C | 0.30 | f 0.20<br>i 0.10 | 26 |
| 13 | C | 0.10 | j 0.25<br>k 0.30<br>l 0.30 | 20 |
| 14 | C | 0.20 | j 0.25<br>k 0.20<br>l 0.30<br>j 0.25 | 22 |

Table 5-continued

| Comparative example | Kind and amount (part) of anti-deteriorating agent | | Kind and amount (part) of stabilizer (antioxidant) | | Induction period (min) |
| --- | --- | --- | --- | --- | --- |
| 15 | C | 0.30 | k | 0.20 | 14 |
| | | | l | 0.30 | |

EXAMPLES 33 – 36

1. Preparation of test piece

Into the same Brabender plasograph as employed in Example 1 which was adjusted to 60 r.p.m. of rotation speed and a temperature of 190°C were charged 100 parts of isotactic polypropylene with no additives (M.I. = 5). Two minutes later, an anti-deteriorating agent and stabilizers (or antioxidants) were added thereto. Another 2 minutes later, 2.3 parts of copper powder were added to the mixture, which was subsequently kneaded for 8 minutes. The mixture was then heated on a plate of 200°C for 1 minute and pressed at a pressure of 300 kg/cm² for 1 minute by means of a spacer to form a film having a thickness of 1.0 mm. The film was cut to give five pieces of 50 mm by 30 mm each.

2. Determination of anti-deteriorating effect

The five test pieces obtained above were kept in Geer's oven (inside temperature: 150° ± 1°C), and periods (in hours) until the test pieces turned yellow and deteriorated were measured and adopted as "Heat stable duration". The results thus obtained are shown in Table 6, in which "Heat stable duration" was indicated with reference to both a piece showing the shortest period and a piece showing the longest period.

Table 6

| Example | Kind and amount (part) of anti-deteriorating agent | | Kind and amount (part) of stabilizer (antioxidant) | | Heat stable duration (hr) |
| --- | --- | --- | --- | --- | --- |
| 33 | H | 0.10 | g | 0.05 | 588 |
| | | | i | 0.40 | ~652 |
| | | | m | 0.15 | |
| 34 | H | 0.20 | g | 0.05 | 720 |
| | | | i | 0.30 | ~795 |
| | | | m | 0.15 | |
| 35 | H | 0.30 | g | 0.05 | 600 |
| | | | i | 0.20 | ~648 |
| | | | m | 0.15 | |
| 36 | H | 0.40 | g | 0.05 | 240 |
| | | | i | 0.10 | ~260 |
| | | | m | 0.15 | |

COMPARATIVE EXAMPLES 16 – 19

Test pieces were prepared by the method described in Example 33 except for using anti-deteriorating agents described in Table 7. Their effects were determined in the manner described in Example 33, and their results are shown in Table 7.

Table 7

| Comparative example | Kind and amount (part) of anti-deteriorating agent | | Kind and amount (part) of stabilizer (antioxidant) | | Heat stable duration (hr) |
| --- | --- | --- | --- | --- | --- |
| 16 | d | 0.10 | g | 0.05 | 490 |
| | | | i | 0.40 | ~525 |
| | | | m | 0.15 | |
| 17 | d | 0.20 | g | 0.05 | 493 |
| | | | i | 0.30 | ~540 |
| | | | m | 0.15 | |
| 18 | d | 0.30 | g | 0.05 | 450 |
| | | | i | 0.20 | ~494 |
| | | | m | 0.15 | |
| 19 | d | 0.40 | g | 0.05 | 168 |
| | | | i | 0.10 | ~202 |
| | | | m | 0.15 | |

What is claimed is:

1. A polyolefin composition which comprises 100 weight parts of a polyolefin selected from the class consisting of homopolymers and copolymers of ethylene, propylene, butene-1, isobutene, pentene-1 and 4-methylpentene-1, copolymers of these olefins and ethyl acrylate, copolymers of these olefins and vinyl acetate, mixtures of these polymers, liquid amorphous polypropylene and liquid amorphous polybutene, and 0.001 ~5 weight parts of N-(salicyloylamino)imide represented by the formula or in which A represents a group in which $R_1 - R_4$ represent hydrogen atoms, halogen atoms, nitro groups, amino groups, carboxyl groups, hydroxyl groups, phenyl groups, phenylthio groups, or straight or branched alkyl, halogenated alkyl, alkoxyl, alkylthio, alkylamino or acylamino groups each having 1 to 5 carbon atoms, and B represents a group in which Q represents an oxygen atom, a sulfur atom, a methylene group, a carbonyl group, a phenylene group, a phthaloyl group, an isophthaloyl group or a terephthaloyl group, and n is an integer of 0 or 1 or 2. The polyolefin composition as claimed in claim 1, in which N-(salicyloylamino)imide is represented by the formula in which A is the same as defined in claim 1.

3. The polyolefin composition as claimed in claim 1, in which N-(salicyloylamino)imide is represented by the formula in which B is the same as defined in claim 1.

4. The polyolefin composition as claimed in claim 2, in which A of the formula of N-(salicyloylamino)imide represents a group in which $R_1 - R_4$ represent hydrogen atoms, halogen atoms, nitro groups, amino groups, carboxyl groups, hydroxyl groups, phenyl groups, phenylthio groups, or straight or branched alkyl, halogenated alkyl, alkoxyl, alkylthio, alkylamino or acylamino groups each having 1 to 5 carbon atoms.

5. The polyolefin composition as claimed in claim 2, in which A of the formula of N-(salicyloylamino)imide represents a group

6. The polyolefin composition as claimed in claim 2, in which A of the formula of N-(salicyloylamino)imide represents a group 7. The polyolefin composition as claimed in claim 2, in which A of the formula of N-(salicyloylamino)imide represents a group 8. The polyolefin composition as claimed in claim 2, in which A of the formula of N-(salicyloylamino)imide represents a group 9. The polyolefin composition as claimed in claim 4, in which all of $R_1 - R_4$ of the formula represent hydrogen atoms.

10. The polyolefin composition as claimed in claim 4, in which all of $R_1 - R_4$ of the formula represent chlorine atoms.

11. The polyolefin composition as claimed in claim 4, in which one of $R_1 - R_4$ of the formula represents a carboxyl group and the others represent hydrogen atoms.

12. The polyolefin composition as claimed in claim 3, in which B of the formula of N-(salicyloylamino)imide represents a group 13. The polyolefin composition as claimed in claim 3, in which B of the formula of N-(salicyloylamino)imide represents a group 14. The polyolefin composition as claimed in claim 1 which comprises 100 weight parts of polyolefin and 0.05 ~ 2 weight parts of the N-(salicyloylamino)imide.

15. The polyolefin composition as claimed in claim 1, which further comprises not less than one kind of a phenolic antioxidant.

16. The polyolefin composition as claimed in claim 15, in which the phenolic antioxidant is selected from the class consisting of
  tetrakis-[methylene 3-(3,5-di-tert-butyl-4-hydroxyphenyl)propionate]methane,
  4,4'-thiobis(3-methyl-6-tert-butylphenol),
  1,3,5-trimethyl-2,4,6-tris(3,5-di-tert-butyl-4-hydroxybenzyl)benzene,
  1,1,3-tris(2-methyl-4-hydroxy-5-tert-butylphenyl)butane,
  octadecyl 3-(3,5-di-tert-butyl-4-hydroxyphenyl)propionate and
  2,6-di-tert-p-cresol.

17. The polyolefin composition as claimed in claim 1, which further comprises not less than one kind of additives which are selected from the class consisting of a known stabilizing agent, dispersing agent, plasticizer and filler.

18. The polyolefin composition as claimed in claim 1, in which the polyolefin is selected from the class consisting of homopolymers and copolymers of olefins.

19. The polyolefin composition as claimed in claim 1, in which the polyolefin is selected from the class consisting of an ethylene homopolymer, isotactic polypropylene and an ethylenevinyl acetate copolymer.

* * * * *